United States Patent [19]
Auth et al.

[11] Patent Number: 4,582,057
[45] Date of Patent: * Apr. 15, 1986

[54] FAST PULSE THERMAL CAUTERY PROBE

[75] Inventors: David C. Auth, Bellevue; Dale M. Lawrence, Lynnwood; Tim R. Majoch, Tacoma, all of Wash.

[73] Assignee: Regents of the University of Washington, Seattle, Wash.

[*] Notice: The portion of the term of this patent subsequent to May 22, 2001 has been disclaimed.

[21] Appl. No.: 553,855

[22] Filed: Nov. 21, 1983

Related U.S. Application Data

[63] Continuation of Ser. No. 285,366, Jul. 20, 1981, Pat. No. 4,449,528, which is a continuation-in-part of Ser. No. 131,897, Mar. 20, 1980, abandoned.

[51] Int. Cl.$^4$ .............................................. A61B 17/36
[52] U.S. Cl. ................................. 128/303.1; 219/229; 219/241; 219/501
[58] Field of Search ............ 128/303.1, 303.13, 303.14, 128/303.17, 303.18, 399–401; 219/229, 230, 233, 240, 241, 242, 501

[56] References Cited

U.S. PATENT DOCUMENTS

| | | | |
|---|---|---|---|
| 2,430,666 | 11/1947 | Burger | 219/233 |
| 3,358,152 | 12/1967 | Alexakis | 219/501 X |
| 3,782,366 | 1/1974 | Brown | 219/240 X |
| 4,301,357 | 11/1981 | Huffman | 219/240 X |

OTHER PUBLICATIONS

Protell et al., "The Heater Probe . . . ", Gastroenterology, 74:257–262, 1978.

Primary Examiner—Lee S. Cohen
Attorney, Agent, or Firm—Seed and Berry

[57] ABSTRACT

A miniaturized, endoscopically deliverable thermal cautery probe for cauterizing internal vessels. The probe is applied to tissues cold, and a large number of electric heating pulses of equal energy are then applied to an internal heating element in the probe. The probe has an internal heating element in direct thermal contact with an active heat-transfer portion that has a low heat capacity to insure quick heating and subsequent cooling, thereby adequately coagulating tissue while minimizing heat penetration and resulting tissue damage. The electrical power applied to the probe is continuously measured and is terminated when the energy delivered reaches a preset value. The number of such pulses applied to the probe (and hence the total energy delivered) may be preset while the duration of the period during which the pulses were applied is displayed. Alternatively, the duration of the period during which such pulses are applied to the probe may be preset while the number of pulses applied (and hence the total energy delivered) is displayed. The heating element for the probe is a controlled breakdown diode which has a breakdown voltage that is a function of its temperature so that the temperature can be controlled. The heating element has a resistance of greater than 0.5 ohm to provide adequate power dissipation with relatively low currents. A washing fluid, preferably flowing along the outside of the probe toward its tip, cleans blood from the tissue to be coagulated to make the source of blood more readily visible.

5 Claims, 7 Drawing Figures

FAST PULSE THERMAL CAUTERY PROBE

The invention described herein was made in the course of work under a grant or award from the U.S. Department of Health, Education and Welfare. The U.S. Government has rights in the invention pursuant to Contract No. NO1 AM-5-211 and Research Project Grant RO1 GM-2526.

CROSS-REFERENCE TO RELATED APPLICATION

This application is a continuation of U.S. patent application Ser. No. 285,366, filed July 20, 1981, now U.S. Pat. No. 4,449,528, which is a continuation-in-part of U.S. patent application Ser. No. 131,897 filed March 20, 1980 and now abandoned.

TECHNICAL FIELD

This invention relates to the coagulation of vascularized tissues, and more particularly to a miniaturized thermal cautery probe which is endoscopically deliverable and which applies precisely controlled heat to such tissues during a relatively short period.

BACKGROUND PRIOR ART

The use of heat for the cauterization of bleeding wounds dates back to ancient times. Perhaps the simplest and most basic thermal cauterization technique involves the application of a hot iron to a bleeding wound. While this technique is somewhat effective in cauterizing large, external wounds, the technique is not applicable to internal wounds. Nor is the technique sufficiently precise or delimited to provide adequate cauterization without excessive tissue damage.

In the present century, the use of radio frequency electric current traveling through a portion of the body has been widely used to stop bleeding. The essential ingredient in radio frequency cauterization is the dissipation of electrical energy in resistive tissue. This dissipated electrical energy is converted into heat, which produces a rise in temperature of the tissue and blood. The plasma proteins in blood are denatured in a temperature range of from 50° to 100° C., producing a sticky or congealed mass of protein. This process is familiar in the cooking of egg white. Other processes may take place when tissue is heated. For example, vessels may contract or shrink, thereby further reducing the flow of blood.

Several radio frequency current generators are now commercially available and are widely used by surgeons for both cutting and coagulating tissue. Since the electrical current flow follows the path of least resistance, the resulting thermal damage, or necrosis, may at times be unpredictable, too deep and uncontrolled. The rationale for using radio frequency current for bleeding control is that the frequency is above that which would cause neuromuscular stimulation and yet permit sufficient power dissipation to produce a rapid rise in temperature. Thus, used properly, electrical shock does not occur and coagulation is accomplished.

There is currently much interest in the control of bleeding using the modern fiberoptic endoscope, which permits visualization and therapy in hollow organs of the body through a slender tube. Hollow channels with a few millimeters of inside diameter permit the insertion of instruments for the administration of therapy such as the coagulation of bleeding. Some investigators have reported good success using radio frequency coagulation through the endoscope in a clinical setting. But this technique has not been widely used in practice because of its inherent risks. Several groups have directed a laser beam through an endoscope using a special optical wave-guide with good success in both animals and humans. However, the high cost of laser coagulators and the as-yet unproven benefit in a controlled clinical trial are slowing the widespread adoption of this technique. Other problems associated with laser coagulators arise from the difficulty in precisely directing the laser beam to a moving target, the existence of optical hazards and the need for a gas injection system to wash away overlying blood. Furthermore, simple laser coagulators do not simultaneously apply heat and pressure to the wound; and the combination of heat and pressure is considered to be more effective than heat alone.

More recently, a miniaturized thermal probe has been developed which is endoscopically deliverable. This probe, which is described in an article by Protell, et al., "The Heater Probe: A New Endoscopic Method for Stopping Massive Gastro-Intestinal Bleeding" *Gastroenterology*, 74: 257–62 (1978), includes a heating coil mounted in a small cylindrical body with a thermocouple. The output of the thermocouple is compared to a temperature reference level, and the difference is used to control the power to the probe to achieve a preset probe temperature. In use, the probe is heated to the preset value and applied to the wound for a number of periods, each of approximately one second in duration. Alternatively, the cold probe is applied directly to the bleeding site, turned on and held there for a predetermined period after reaching a target temperature. The principal problem associated with the latter technique is the inability of the probe to reach coagulating temperature with sufficient speed and to then cool itself with sufficient speed to prevent excessive penetration of the heat by diffusion. Effective coagulation requires that the bleeding site be adequately heated. However, avoidance of thermal necrosis requires that the heat not penetrate too deeply. The only technique providing adequate heating of the bleeding site without producing excessive heat penetration is heating the bleeding site at a high temperature for an extremely short period of time. Presently existing thermal probes are not able to meet these requirements. The problem does not stem from an inability to heat the probe with sufficient speed as much as it does from an inability to cool the probe with sufficient speed. Any probe can be heated rapidly by merely utilizing a sufficiently larger heater. However, the probe can be cooled only by the tissue with which it is in contact. Conventional probes have been incapable of being cooled by the surrounding tissue with sufficient speed due to their relatively high thermal mass.

Attempts have been made to design thermal cautery probes which are heated by passing a current through the body of the probe itself instead of through a separate heating element. An example of such probes is disclosed in U.S. Pat. No. 3,886,944, issued to Jamshidi. The disadvantages of such probes are twofold: first, the unavailability of a satisfactory probe material and, second, the nonuniformity of the probe temperature.

The choice of a probe material presents a problem because the resistance of the material must be high enough to dissipate sufficient power and the strength of the material must be high enough to withstand forces applied to the probe by the tissue and other objects. The Jamshidi probe utilizes a Nichrome alloy or stainless steel as the probe material. Either material has a relatively low resistivity, thereby making it difficult for the probe to dissipate sufficient power without applying a great deal of current to the probe. While probes requiring high current are acceptable under some circumstances, they are uncceptable where the probe is to be endoscopically deliverable since the high currents require wires which are larger than the endoscope channels. In fact, a probe having a resistance less than about 0.5 ohm will generally require more current than endoscopically deliverable power leads are capable of carrying.

A probe fabricated of a low-resistivity material can dissipate adequate power from relatively low current only by making the material extremely thin so that the resistance of the probe is high. Yet a probe having an extremely thin shell does not have sufficient strength to withstand clinical use.

A probe having a relatively thick shell of a higher resistivity or semiconductive material would be capable of dissipating adequate power at acceptably low currents. However, a material having these properties and which is inexpensive, easily worked, and sufficiently sturdy does not appear to be available.

The second disadvantage mentioned above—the non-uniformity of probe temperature—is illustrated in the Jamshidi patent. In the Jamshidi probe, current flows outwardly from the center of the probe tip and then along the sides of the probe. The current density—and hence the power dissipation—varies from a maximum at the center of the probe to a minimum at the sides of the probe. As a result, the temperature of the probe decreases from a maximum at the center of the probe.

DISCLOSURE OF THE INVENTION

The primary object of the invention is to provide a thermal cautery probe having a heat capacity which is sufficiently low to allow rapid heating and cooling, thereby effectively coagulating vascularized tissue without undue thermal necrosis.

It is another object of the invention to provide a thermal probe which is powered for a predetermined period while measuring and displaying the total energy delivered to the probe during that period.

It is another object of the invention to provide a thermal cautery probe which is powered by a relatively low current.

It is another object of the invention to provide a low thermal mass cautery probe which has a uniform temperature distribution.

It is still another object of the invention to provide a thermal probe which receives a predetermined value of energy while measuring and displaying the duration of the period during which the energy is delivered.

It is yet another object of the invention to provide a low heat capacity cautery probe which receives energy over a relatively short period in the form of a large number of relatively short, equal energy pulses.

It is another object of the invention to provide a heating element for a thermal cautery probe which inherently provides an indication of the temperature of the probe's active heat transfer portion.

It is a further object of the invention to provide a washing system for a thermal cautery probe which effectively washes blood from the wound without interfering with cauterization, thereby facilitating identification of the bleeding site.

It is a still further object of the invention to provide a thermal cautery probe which does not have a tendency to adhere to coagulated tissue.

These and other objects of the invention are provided by an electrically powered thermal probe including an active heat-transfer portion having a low heat capacity which is in direct thermal contact with a heating element so that heat is transferred principally by conduction. The probe is heater active during a heating period having a duration of less than five seconds. Yet sufficient power is applied to the heat-transfer portion during the heating period to coagulate tissue, and the low heat capacity of the heat-transfer portion allows rapid cooling after the heating period. The effective impedance of the heater is greater than 0.5 ohm so that the heater can be powered through power lines that are capable of extending through the channels of an endoscope. The energy is delivered in the form of a large number of relatively short pulses, each delivering the same quantity of energy to the probe. The probe may be used in either of two modes. In a first mode the energy to be delivered to the probe is preset and the duration of the period during which the pulses are delivered is displayed. Accordingly, a down-counter is preset to a number indicative of the energy to be delivered, and each heating pulse decrements the down-counter until a zero count is reached. During this period, an oscillator is gated to an up-counter and the contents of the counter is displayed to indicate the duration of the period during which the heating pulses were delivered. In a second mode, the duration of the period that the heating pulses are applied to the probe is preset, and the energy delivered to the probe is displayed. Accordingly, the down-counter is preset to a number indicative of the period during which the pulses are to be delivered, and an oscillator is gated to the down-counter when the pulses are being delivered until a zero count is reached. Meanwhile, the heating pulses are applied to the up-counter, and the contents of the counter is displayed to indicate the energy delivered to the probe during the heating period. The heating element for the probe is preferably a controlled breakdown diode, such as a zener or avalanche diode, which provides good heat dissipation at low currents and has a breakdown voltage which is temperature dependent so that it provides an electrical indication of probe temperature. The probe temperature indication is used to inhibit the delivery of heating pulses to the probe where the temperature of the probe exceeds a target value. A plurality of water jets, which are circumferentially spaced about the body of the probe, direct water along the probe sidewalls in an axial direction, thereby clearing blood from the bleeding site. Finally, the end of the probe is coated with a special compound to prevent the probe from adhering to coagulated tissues.

In operation, one of the two operating modes is selected and the cauterization time or cauterization energy is preset, depending upon which mode is selected. The probe is then applied to the wound while cold, and a switch is activated to apply power to the probe. The low heat capacity of the probe's active heat-transfer portion allows it to quickly reach a sufficient temperature to effectively cauterize the wound and to rapidly cool after power is removed to prevent excessive thermal penetration, thereby minimizing necrosis.

BRIEF DESCRIPTION OF THE DRAWINGS

FIG. 4 A and B is a schematic of the circuitry for supplying power to the thermal cautery probe;

BEST MODE FOR CARRYING OUT THE INVENTION

Figure 1:
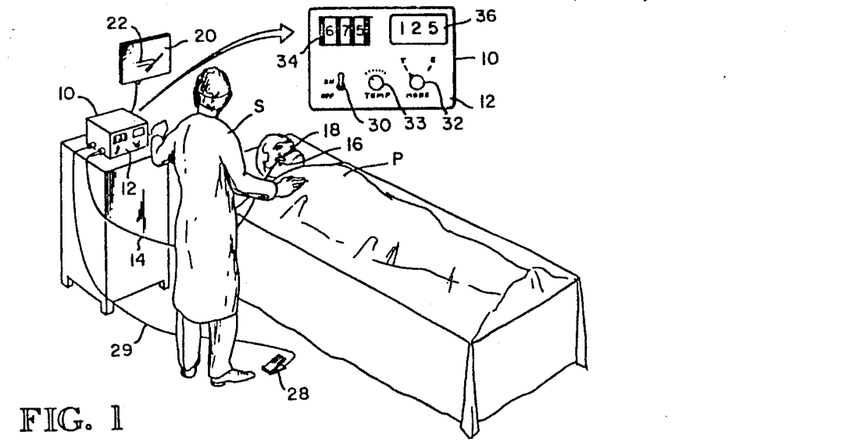
FIG. 1 is an isometric view of the fast pulse thermal cautery probe in operation.

The fast pulse thermal cautery probe is illustrated in use in FIG. 1. The probe includes a power supply and display unit 10 having a front panel 12 containing switches and indicators illustrated in greater detail in the enlarged view. A specially constructed catheter 14 extends from the power supply and display unit 10 to a headpiece 16 of a conventional fiberoptic endoscope 18 extending into the mouth of a patient P to, for example, the patient's stomach. The headpiece 16 typically includes an eyepiece through which a surgeon S views internal cavities. However, the headpiece 16 may alternatively interface with various optical devices of conventional design. These devices may produce an image on a screen 20 of the position of the probe 22 within the stomach of the patient P. The endoscope 18 typically includes one or more passages or channels extending in parallel with the fiberoptic wave guide to allow various devices to be inserted into internal organs of a patient. The catheter 14 extends through one of these channels to the end of the endoscope 18 within an internal organ. A surgeon S may then position the probe 22 against a lesion such as an ulcer by manipulating actuator knobs generally positioned on the headpiece 16 of conventional endoscopes 18. The endoscope channels are necessarily limited in diameter so that the diameter of the power leads for applying power to the probe are also limited. In practice, the diameter of the power leads is limited to a size which is capable of delivering sufficient current for cauterization to a probe having a resistance of at least about 0.5 ohm. A probe having a lower resistance must receive a current which is in excess of that which endoscopically deliverable power leads are capable of efficiently carrying without producing excessive heating of the endoscope.

A foot switch 28 is also connected to the power supply and display unit 10 through a lead 29. As explained in greater detail hereinafter, the surgeon S actuates the foot switch 28 to apply power to the probe 22 after the probe has been applied to the lesion. A second switch, operating in conjunction with the switch 28, may be actuated to supply a washing fluid to the probe.

As best illustrated in the enlarged view of FIG. 1, the panel 12 includes an on-off switch 30 for applying power to the unit 10 and a mode switch 32 for selecting either a "time" mode or an "energy" mode. In the time mode, heating pulses are applied to the probe 22 for a period having a duration determined by the number preset with conventional thumb wheel switches 34. At the end of the period, the total energy delivered to the probe 22 during that period is shown on a conventional digital indicator 36. In the energy mode, the energy to be delivered to the probe each time the switch 28 is activated is seleted by the thumb wheel switches 34, and the duration of the period during which the pulses are delivered is shown on the indicator 36. The temperature of the probe during the heating period in either mode is selected by a temperature control knob 33.

Figures 2, 3:
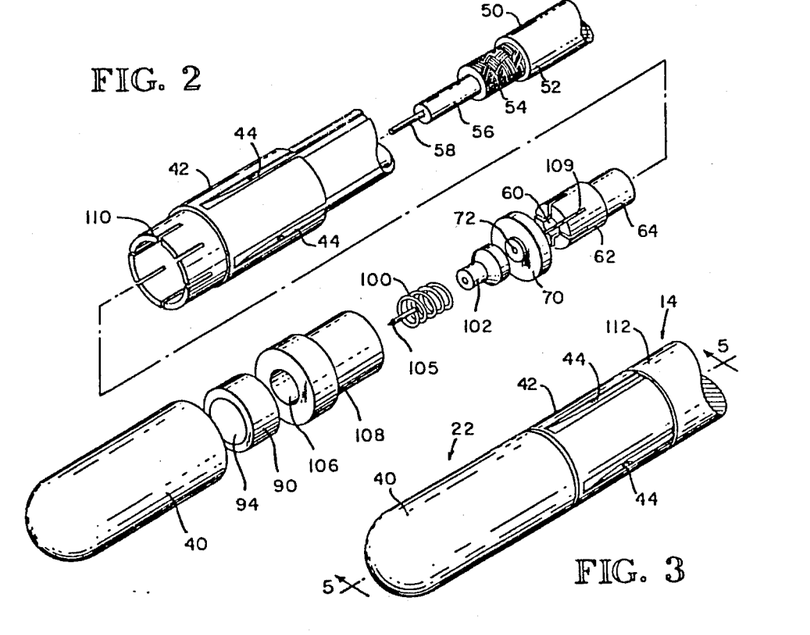
FIG. 2 is an exploded isometric view of the thermal cautery probe.
FIG. 3 is an isometric view of the assembled thermal cautery probe.

The probe 22 is illustrated in assembled condition in FIG. 3. It is composed of an elongated cylindrical shell 40 having a smooth, round-ended forward portion and a cylindrical body 42 containing a number of circumferentially spaced-apart cleaning fluid nozzles 44. The catheter 14 abuts the body 42 of the probe 22 and supplies cleaning fluid to the nozzles 44 and heating pulses to an internal heating element in the shell 40, as explained in greater detail hereinafter.

Figure 5:
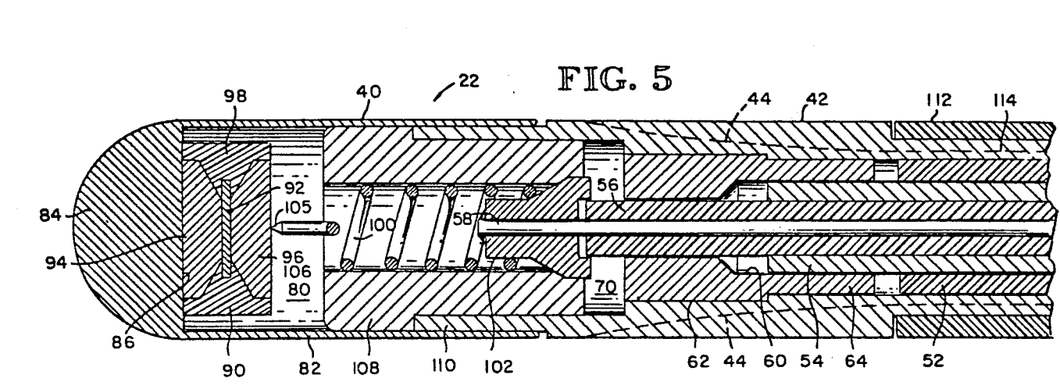
FIG. 5 is a cross-sectional view taken along the line 5—5 of FIG. 3.

The internal structure of the probe 22 is illustrated in greater detail in FIGS. 2 and 5. This structure is best explained in the context of the manufacturing procedure for the probe. Initially, a coaxial cable 50 is prepared by trimming a portion of an insulating sheath 52 back from an underlying coaxial metal braid 54, a coaxial dielectric insulator 56 and a center conductor 58. In a similar manner, the braid 54 is trimmed back from the underlying insulator 56 and conductor 58, and the insulator 56 is trimmed back from the underlying conductor 58. As a result, each component of the cable 50 is accessible.

After the cable 50 has been prepared as explained above, the body 42 of the probe 22 is loosely slipped over the cable 50, and the insulator 56 and center conductor 58 are inserted through a bore 60 of a coaxial braid anchor 62 with the braid 54 loosely fitting inside a cylindrical portion at the rear of the braid anchor 62. The braid 54 is then soldered to the walls of the bore 60 by conventional means to electrically and mechanically connect the braid anchor 62 to the braid 54 of cable 50.

A spring mount 102 is then soldered to the coax center conductor 58 and a spring 100 is soldered onto the spring mount 102. Next, the braid anchor 62 is slipped into the body 42 with resilient fingers 109 of the braid anchor 62 frictionally engaging the inside surface of the body 42. Next the assembly is placed in a vertical position and a small amount of epoxy is applied between spring mount 102 and braid anchor 62 to form a seal 70 having a shoulder 72. The seal 70 provides electrical insulation and a seal to prevent fluids from entering the internal cavity of the probe. A teflon seal 108 is then pressed into body 42 with the shoulder on seal 108 resting against the fingers 110 of body 42. The spring 100 now lies inside of the cylindrical bore 106 of seal 108 with the axial tip 105 of spring 100 protruding from the bore 106 a small amount.

After the rearward components of the probe 22 are prepared and assembled as explained above, the internal components of the shell 40 are assembled. As best illustrated in FIG. 5, the shell 40 is generally hollow to form a cylindrical cavity 80 surrounded by thin, cylindrical side walls 82. The front end of the shell 40 is a solid hemispherical heat transfer portion 84 having a planar, circular rear face 86. A controlled breakdown diode, such as a zener or avalanche diode 90, is then bonded within the cavity 80 against the rear face 86. The diode 90 includes a diode chip 92, a pair of cylindrical conductors 94, 96 connected to opposite faces of the diode chip 92, and an insulative coating 98 surrounding the diode chip 92 and conductors 94, 96. Although a diode 90 having the structure shown could be specially fabricated, the diode 90 is preferably formed by severing the ends of commercially available diodes having a cylindrical shape. A simpler and easier technique would be to solder a commercially available diode chip directly to cavity 80 against the rear face 86, although other heating devices such as a thin film resistor or conventional diode, may also be used. However, such alternative heating devices generally require substantially more current to dissipate the same amount of power. For example, a 14-volt zener diode dissipates about twenty times more power for a given current than a diode having 0.7-volt forward breakdown voltage.

The diode 90 is mounted in the shell 40 by first tinning the rear face 86 of the heat transfer portion 84 with solder. The exposed surface of one diode conductor 94 is then also tinned and placed in the shell 40, preferably using an alignment jig to position the diode 90 at the center of the shell 40. The shell 40 is then heated to fuse the solder on the rear face 86 and the solder on the diode conductor 94. The diode 90 is thus in direct thermal contact with the heat-transfer portion 84 so that heat is transferred from the diode 90 to the heat-transfer portion 84 principally by conduction rather than by radiation.

After the diode 90 is soldered within the shell 40, the outer surfaces of the shell 40 are polished and then plated with copper and gold. Finally, a conformal coating is applied to the outer surface of the shell 82 to prevent it from sticking to tissues after coagulation. The coating is preferably Type R-4-3117 sold by Dow-Corning which is normally used to seal printed circuit boards from moisture and abrasion. The coating should be applied over an undercoat of Dow Corning 1204 Primer for best adhesion of the conformal coating to the probe. Alternatively, the primer may be used without the conformal coating, providing the probe with better heat transfer characteristics to tissue but having a greater tendency to adhere to coagulated tissues.

In a final assembly stage, the shell 40 is moved rearwardly until resilient fingers 110 of the body 42 frictionally engage the inner walls 82 of the shell 40. Finally, as illustrated in FIGS. 3 and 5, a catheter 112, loosely surrounding the cable 50, is slipped onto a shoulder 114 (FIG. 5) formed along the rear edge of the body 42, thereby completing the assembly of the probe.

A washing fluid is pumped through the catheter 112 around the cable 50 and enters rear openings of the nozzles 44. The washing fluid then flows along the side of the shell 40 in an axial direction to wash blood from the lesion, thereby facilitating the identification of bleeding sites in need of coagulation. A variety of commercially available pumps may be used to deliver washing fluid to the probe. However, the fluid is preferably delivered in a pulsating fashion to allow sufficient bleeding between washing pulses to make the site of bleeding readily visible.

It is highly advantageous to run the washing fluid along the outside of the shell for a number of reasons. First, the washing fluid does not pass between the heat transfer portion 84 of the probe and the tissue to be coagulated. Consequently, it does not interfere with the transfer of heat from the probe to the tissue. Second, the washing fluid flows along surfaces which do not contact tissue and are thus not susceptible to tissue clogging which would interfere with fluid flow. Finally, the fluid stream is spread out over a sufficiently large area to prevent tissue damage which might otherwise occur with a more concentrated fluid stream.

In the probe's assembled condition, the conductor spring 100 is somewhat compressed so that the point 105 forcibly contacts the conductor 96. The diode conductor 94 is connected to the shell 40 and, in turn, to the braid 54 through the body 42 and braid anchor 62. Thus, as current pulses are applied between the center conductor 58 and the braid 54 of cable 50, current flows through the semi-conductor junction 92, which quickly heats the heat transfer portion 84. Because of the low heat capacity of the heat transfer portion 84, the portion 84 not only quickly rises to a target temperature, but it also quickly cools after heating pulses are no longer applied to the probe 22.

Figure 4A:
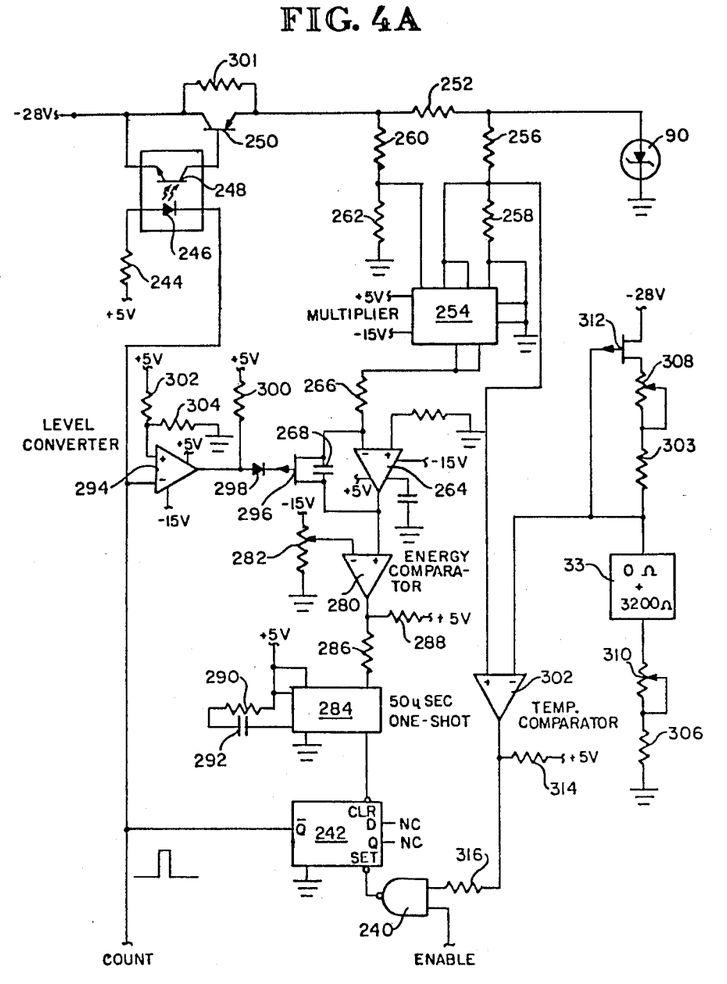
Figure 4B:
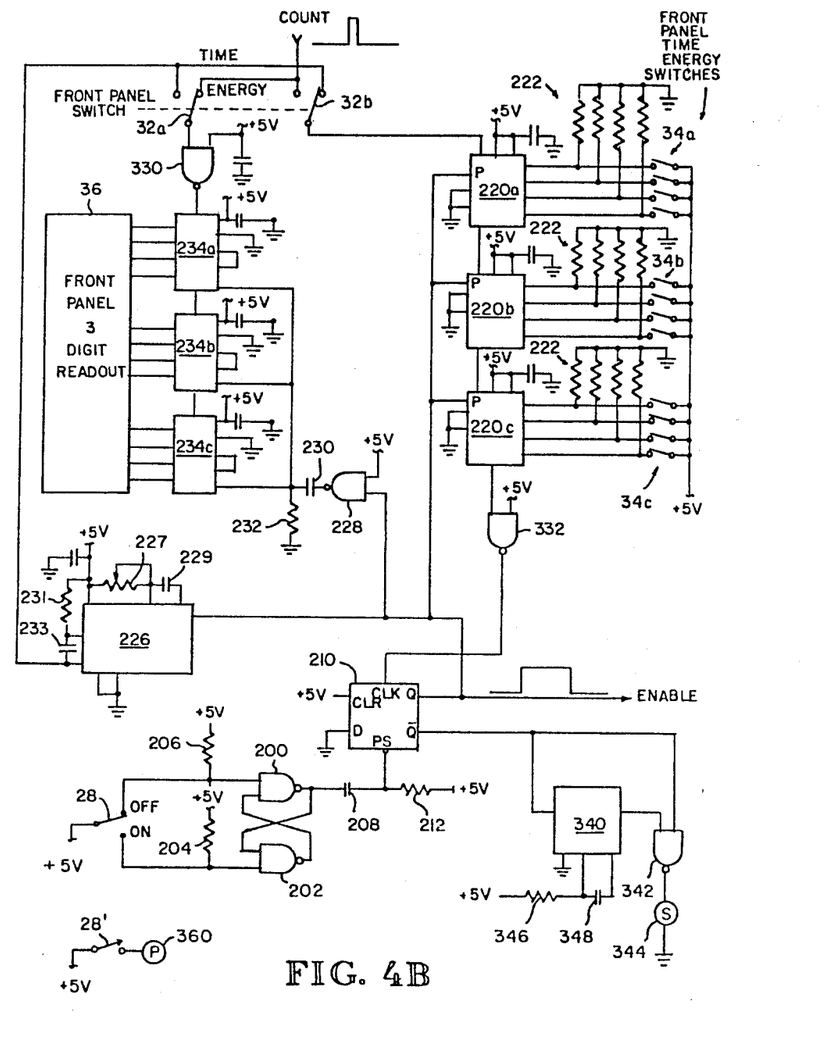

The circuitry for generating the heating pulses is illustrated in FIGS. 4A and 4B. With reference first to FIG. 4B, the foot switch 28, in its "off" position, places a logic low at one input to a set-reset flip-flop formed by NAND gates 200, 202. Consequently, the output of NAND gate 200 is high, while the output of NAND gate 202 is low since its other input is biased high through resistor 204. When the switch 28 is moved from the "off" position, the output of NAND gate 200 is held high by the low at the output of NAND gate 202 since its other input is biased high through resistor 206. When the switch 28 is actuated to the "on" position, the output of NAND gate 202 goes high, thereby causing the output of NAND gate 200 to go low. The negative-going transition at the output of NAND gate 200 is differentiated by capacitor 208 and applied to the preset (ps) terminal of flip-flop 210, which is normally held high through resistor 212. The Q output of flip-flop 210 then goes high to produce an ENABLE signal. It will be noted that a negative-going transition will not be generated at the output of NAND gate 200 until the switch 28 is returned to its "off" position and once again cycled to its "on" position. Consequently, any contact bounce present in switch 28 as the switch reaches its "on" position, has no effect on the operation of the circuit.

The ENABLE signal generated by flip-flop 210 has a number of functions. First, it presets cascaded counters 220a,b,c with numbers selected by the thumbwheel switches 34a, b,c, respectively. The data inputs to these counters 220 are normally held low through resistors 222, but these lines are driven high by the switches 34 so that the BCD numbers applied to each of the counters 220a,b,c correspond to the decimal numbers appearing on the panel 12 of the power supply and display unit 10.

The enable input also enables a synchronous oscillator 226 formed by a one-shot, which generates a pulse train having a frequency determined by the time constant of resistor 227 and capacitor 229 and the time constant of resistor 231 and capacitor 233. The ENABLE signal is also inverted by enabled NAND gate 228 to produce a negative-going transition which is differentiated by capacitor 230 and resistor 232 to generate a negative-going reset pulse which resets counters 234a,b,c. Thus, actuation of the foot switch 28 resets up-counters 234a,b,c, presets down-counters 220a,b,c with a number selected by thumb wheel switches 34a,b,c and allows oscillator 226 to begin decrementing the down-counters 220a,b,c.

With reference now to FIG. 4A, the ENABLE signal is also applied to NAND gate 240 to initiate the delivery of heating pulses to the probe 22. Assuming that the other input to NAND gate 240 is high, the low to high transition of the ENABLE signal sets flip-flop 242 so that its $\overline{Q}$ output goes low. Current then flows through resistor 244 and light-emitting diode 246. The light-emitting diode 246 is optically coupled to a phototransistor 248 which saturates to drive transistor 250 to saturation so that a negative power supply voltage is applied directly to the diode 90 through a fairly low impedence resistor 252. The voltage supplied to the diode 90 is applied to a conventional integrated circuit multiplier 254 after being attenuated by resistors 256, 258 arranged in a voltage divider configuration. The voltage on the opposite terminal of the resistor 252 (which exceeds the voltage on diode 90 by a function of the current-through diode 90) is similarly applied to the multiplier 254 after being attenuated by resistors 260, 262 arranged as a voltage divider. The multiplier 254 generates a voltage which is proportional to the product of the voltage applied to the diode 90 and the voltage across the resistor 252. Since the voltage across resistor 252 is proportional to the current-through diode 90, the voltage at the output of the multiplier 254 is proportional to the power being applied to the diode 90. This power signal is applied to an operational amplifier 264 through resistor 266. The operational amplifier has a capacitor 268 connected in its feedback path so that it operates as an integrator. The integrated power signal at the output of the amplifier 264 is thus a voltage proportional to the energy which has been delivered to the diode 90 from the end of the last COUNT pulse. The energy signal at the output of amplifier 264 is compared by a comparator 280 to an energy reference signal generated by potentiometer 282. When the energy delivered to the diode 90 exceeds a value determined by the potentiometer 282, the output of the comparator 280 goes low, thereby actuating a one-shot 284 through resistor 286. The trigger input to the one-shot 284 is normally held high through resistor 288 and the resistor 286. The one-shot 284 clears or disables the flip-flip 242 for a predetermined period determined by the time constant or resistor 290 and capacitor 292.

During this disabling period, the $\overline{Q}$ output of flip-flop 242 is high, thereby causing amplifier 294 to clip at its negative supply level. This negative voltage back-biases diode 298, thereby floating the gate of FET transistor 296. The source to drain impedance of the FET 296 is then greatly reduced, thereby discharging capacitor 268 and reducing the output of the power signal integrator 264 to zero volts. At the end of this COUNT pulse (after the disable period as determined by one-shot 284), the $\overline{Q}$ output of flip-flop 242 once again goes low, causing the output of amplifier 294 to float so that the gate of FET 296 is held high through resistor 300. The source to drain impedance of the FET 296 then increases sufficiently to allow the amplifier 264 to once again integrate the incoming power signal. The amplifier 294 thus functions as a level converter to interface the logic circuitry of the flip-flop 242 to the voltage levels required by the FET 296. It switches between these two voltage levels at a voltage determined by resistors 302, 304, which are arranged in a voltage divider configuration.

At the end of the fifty microsecond disable period, flip-flop 242 is once again set, thereby once again saturating transistors 248, 250 and applying power to the diode 90. It is thus seen that as long as a logic "0" is applied to the set terminal of flip-flop 242, measured quantities of energy are sequentially applied to the diode 90 in a pulse train.

The foregoing explanation of the circuit operation presupposes that both inputs to NAND gate 240 are logic "1" during the operating cycle. This will always be the case as long as the temperature of the diode 90 is below a preset value. However, NAND gate 240 is disabled as long as the temperature of the diode 90 exceeds the predetermined value. Consequently, the temperature of the probe 22 quickly rises to the predetermined value as current pulses are repetitively applied to the diode 90; and when the predetermined level is reached, the pulses are applied to the diode 90 at a lower frequency to maintain the temperature constant.

In accordance with this feature, a by-pass resistor 301 is positioned between the base and emitter of transistor 250 so that a slight amount of current flows through diode 90 when transistors 248 and 250 are cut off. Diode 90 is preferably an avalanche diode, and its reverse breakdown voltage is proportional to its temperature. Consequently, the voltage between resistors 256 and 258, which is applied to a temperature comparator 302 is a measure of the temperature of the diode 90. This temperature feedback voltage is compared to a reference voltage determined by resistors 303, 306 and potentiometers 308, 310 and the temperature controller potentiometer 33. Potentiometer 308 is varied to adjust the bias on field effect transistor 312, thus adjusting the slope of the temperature-to-voltage transfer curve. The potentiometer 310 is adjusted to set the 0° C. Intercept on the curve, thereby calibrating the temperature selector 33. When the temperature, as indicated by the voltage on the positive input to the comparator 302, exceeds the level set by potentiometer 33, its output goes low so that a low is placed on the input to NAND gate 240 through resistor 316. Thereafter, no additional current pulses can be applied to the diode 90 until the temperature falls below the preset value. The temperature comparator 302 then generates a logic "1" to enable the NAND gate 240.

Returning now to FIG. 4B, when the switch 32a is in the "energy" position as illustrated, the COUNT pulses produced each time a current pulse is applied to the probe 90 are inverted by enabled NAND-gate 330 and applied to the first counter 234a of a series of cascaded counters 234a,b,c. It will be remembered that these counters 234 had been reset to zero by the leading edge of the ENABLE signal when the switch 28 was initially actuated. At the termination of each current pulse to the diode 90, the counters 234 are incremented by a COUNT pulse. Thus, the content of the counters 234 is an indication of the total energy which has been applied to the probe 90 during the ENABLE pulse. The counters 234 drive the front panel three-digit readout 36 which then continuously indicates the energy which has been applied to the probe 90.

As long as the ENABLE signal is present, the oscillator 226 continuously generates timing pulses regardless of the frequency at which current pulses are applied to the diode 90. When the switch 32b is in the time position indicated, these pulses are applied to the first counter 220a of a series of down-counters 220a,b,c. As mentioned above, the leading edge of the ENABLE pulse presets the counters 220 with a number corresponding to the number selected by the thumb wheel switches 34 of the front panel 12. The counters 220 thus begin counting down from this number until a zero count is reached. Upon the zero count from counter 220c, a high is produced at the output of enabled NAND-gate 332 which clocks a logic "0" on the data input (D) of flip-flop 210 to its Q output, thereby terminating the ENABLE pulse. The ENABLE line is now logic "0", thereby disabling the oscillator 226 so that counters 220a,b,c are no longer decrementing. The ENABLE low also removes the low from the set input to flip-flop 242 (FIG. 4A), thereby allowing its $\overline{Q}$ output to remain high in order to prevent COUNT pulses from being generated which would otherwise cause additional current pulses to be applied to the diode 90 and increment the counters 234a,b,c. It is thus seen that when switch 32 is in the "time" position illustrated, the switches 34 select the duration of the period during which current pulses are applied to the probe 90, while the front panel three-digit readout 36 indicates the total quantity of energy delivered to the diode 90 during that period.

Repositioning the switch 32 to the "energy" mode causes the timing pulses from oscillator 226 to be applied to the up-counters 234 while the COUNT pulses generated for each heating pulse are applied to the down counters 220. Thus, in this alternate "energy" mode, the switches 34 select the total energy to be delivered to the diode 90 while the front panel three-digit readout 36 indicates the duration of the period during which the energy was delivered to the diode 90.

During use of the probe 22, the termination of the heating pulses applied to the probe 22 is not visually apparent. Consequently, an audible alarm may be provided to inform the surgeon when to remove the probe from the wound area. Accordingly, as illustrated in FIG. 4B, the $\overline{Q}$ output of flip-flop 210 is applied to a one shot 340 and a NAND-gate 342. The output of the NAND-gate 342 is applied to a conventional audio alarm 344, commonly known as a "SONALERT".

Prior to initiating an ENABLE pulse, the $\overline{Q}$ output of flip-flop 210 and the output of one-shot 340 are both high, keeping the output of NAND gate 342 low so that no current flows through the SONALERT 344. When the ENABLE pulse occurs, NAND gate 342 becomes disabled and its output goes high, turning on the SONALERT 344. At the termination of the ENABLE pulse, the $\overline{Q}$ output of flip-flop 210 goes high, thereby triggering the one-shot 340, whose output goes low, keeping NAND gate 342 disabled despite the high input from the $\overline{Q}$ output of flip-flop 210. When the one-shot 340 output goes high after a period determined by resistor 346 and capacitor 348, the NAND gate 342 is again enabled, setting its output low and turning off the SONALERT 344. Thus, the SONALERT 344 operates during the ENABLE pulse and for a fixed time longer. This added time insures that a complete cycle occurred with the probe in contact with the lesion, including the time required for the probe-tissue interface temperature to fall below that for tissue denaturization. This is generally on the order of about 0.2 second.

The foot switch 28 may also include a second switch contact 28' which, when closed, applies power to a conventional fluid pump 360 which delivers washing fluid to probe. As mentioned above, the pump 360 preferably operates in a pulse-like manner to allow a sufficiently long period between pulses to identify bleeding sites.

In operation, an endoscopist or surgeon first threads the catheter 14 through a channel in an endoscope 18 and manipulates the probe 22 at the end of the catheter 14 until it is in a desired position against the wound. Either thereafter or before, the surgeon S has selected either a time or an energy mode, and he has selected either a predetermined duration of cauterization or cauterization energy, respectively, on thumb wheel switches 34. Finally, the surgeon S rotates temperature potentiometer 33 to select a predetermined temperature. The surgeon then actuates the foot switch 28 to cauterize the wound or deliver washing fluid to the wound. In the time mode, the energy applied to the probe 22 during the heating period is displayed on the readout 36. In the energy mode, the duration of the cauterization period is displayed on the readout 36. The probe 22 is then repositioned a number of times, after which the switch 28 is actuated to cauterize various portions of the wound.

Figure 6:
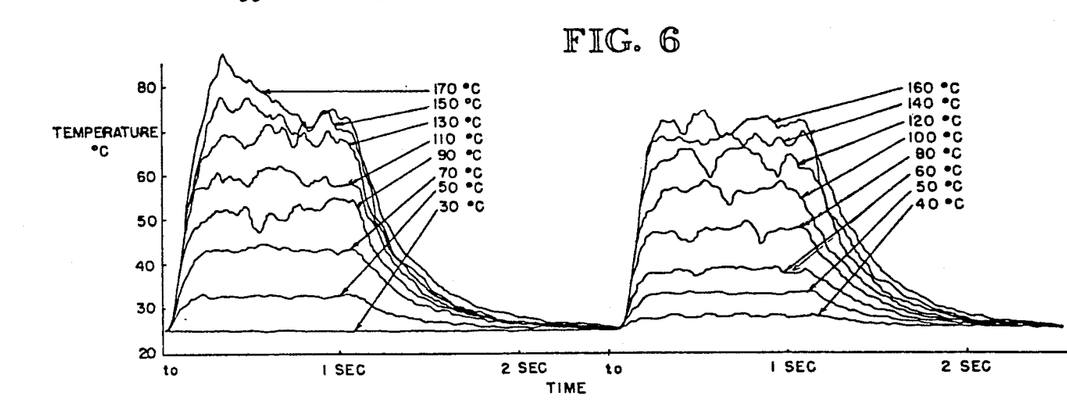
FIG. 6 is a graph showing the temperature at the heat transfer surface of the probe.

The temperature characteristics of the probe may be examined with reference to FIG. 6. As clearly illustrated therein, the probe reaches a target temperature in less than one-fourth of a second, remains fairly constant thereafter, and drops to less than 50 percent of the target value in less than one second. As a result, it is not necessary to leave the probe in contact with the wound for a long period in order to effectively cauterize the wound, so deep thermal penetration, and hence, thermal necrosis, do not occur. It has been found that the temperature of the active heat transfer portion of the probe should be at least 100° C. to provide adequate coagulation in a fairly short time period. It has also been determined that deep heat penetration, and hence thermal necrosis, occurs when a probe having a temperature of at least 40 percent of the required temperature contacts tissue for more than 5 seconds. Thus the probe must be rapidly heated and rapidly cooled within the specified range to adequately coagulate without causing tissue damage. Rapid heating is not difficult because the power consumption of the probe heater can be adjusted as desired. However, probe cooling after the heating period is provided by heat conduction of the tissue contacting the probe. Unlike the problem of rapid heating, rapid cooling can be accomplished only by using a probe having a low heat capacity. It has been determined that the probe requirements for sufficiently rapid heating and cooling can be accomplished with a probe having an active heat transfer portion that has a unit heat capacity of about less than ~1 joule/°C. or, equivalently, a unit heat capacity of less than ~0.25 Cal./°C. Probes having a larger heat capacity run the risk of causing deeper damage if effective coagulation is achieved.

Although the device described herein is principally designed for cauterization, it will be understood that it may also be used for other types of treatment. For example, it may be used to destroy superficial skin cancers without causing deep tissue damage. Consequently, the scope of the invention is not to be limited by the field to which the invention is applied.

We claim:

1. A probe for heating tissue, comprising a probe body having a heat conductive portion forming an external heat-transfer surface adapted to be placed in contact with said tissue, a diode mounted in said probe body in thermal contact with said heat conductive portion so that electricity flowing through said diode generates heat that is conducted through said heat-conductive portion to said heat-transfer surface, said diode having a reverse breakdown voltage that is proportional to its temperature, and a power supply connected to said diode through a conductor, said power supply having a polarity that causes reverse current to flow through said diode, said power supply including means for adjusting the power that said power supply delivers to said diode responsive to variations in the magnitude of said reverse breakdown voltage in order to control the temperature of said probe.

2. The probe of claim 1 wherein said probe body comprises a generally cylindrical, electrically conductive shell having said heat-conductive portion formed at one end and a cylindrical cavity having an opening at the opposite end, and wherein said diode is mounted in said cavity in direct thermal contact with said heat-conductive portion.

3. The probe of claim 2 wherein the diode mounted in said cavity has a pair of opposed planar conductive faces, one of which is soldered to the heat-conductive portion of said shell, said probe further including an electrically conductive spring in electrical contact with the conductor that is connected to said power supply, said spring bearing against the other face of said diode, thereby supplying electrical power to said diode.

4. The probe of claim 1 wherein said heat-transfer surface is coated with a low-adhesion material to prevent said heat-transfer surface from sticking to tissue.

5. The probe of claim 1 wherein said diode is a zener diode so that the power generated by said diode in operation is proportional to the product of the zener voltage of said diode and the current through said diode.

* * * * *